US006762148B2

(12) United States Patent
Ohishi et al.

(10) Patent No.: US 6,762,148 B2
(45) Date of Patent: Jul. 13, 2004

(54) CATALYST PROCESS OF MAKING

(75) Inventors: Junzo Ohishi, Yamaguchi (JP); Masahiro Senyo, Yamaguchi (JP); Yoshimasa Seo, Yamaguchi (JP); Hideki Sugi, Gumma (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/321,955

(22) Filed: Dec. 17, 2002

(65) Prior Publication Data

US 2003/0109381 A1 Jun. 12, 2003

Related U.S. Application Data

(62) Division of application No. 09/830,234, filed on Apr. 24, 2002, now abandoned.

(30) Foreign Application Priority Data

Sep. 17, 1999 (JP) .......................................... 11-262822

(51) Int. Cl.$^7$ ................................................ B01J 23/00
(52) U.S. Cl. ....................... 502/318; 502/305; 502/311; 502/439
(58) Field of Search ................................. 502/305–314, 502/316, 317–323, 439, 104, 110, 113, 117, 248, 255, 407

(56) References Cited

U.S. PATENT DOCUMENTS

| 4,051,180 A | | 9/1977 | Shaw et al. ................. 260/530 |
| 4,093,635 A | * | 6/1978 | Bremer et al. ......... 260/346.75 |
| 4,120,876 A | * | 10/1978 | Bremer et al. ......... 260/346.75 |
| 4,155,938 A | * | 5/1979 | Yamamoto et al. ..... 260/604 R |
| 4,178,464 A | * | 12/1979 | Sakamoto et al. .......... 562/535 |
| 4,186,152 A | * | 1/1980 | Yamamoto et al. ..... 260/604 R |
| 4,246,427 A | * | 1/1981 | Andoh et al. ................ 562/535 |
| 4,251,393 A | * | 2/1981 | Dalton et al. ................ 252/443 |
| 4,259,211 A | * | 3/1981 | Krabetz et al. ............. 252/443 |
| 4,271,040 A | * | 6/1981 | Khoobiar .................... 252/437 |
| 4,272,637 A | * | 6/1981 | Yamamoto et al. ......... 568/780 |
| 4,276,196 A | * | 6/1981 | Dalton et al. ................ 252/435 |
| 4,289,654 A | | 9/1981 | Bertolini et al. ............ 252/456 |
| 4,317,927 A | * | 3/1982 | Dalton et al. ................ 562/535 |
| 4,321,160 A | * | 3/1982 | Farrington et al. ......... 252/437 |
| 4,339,355 A | * | 7/1982 | Decker et al. ............... 252/464 |
| 4,358,608 A | * | 11/1982 | Shaw et al. .................. 562/534 |
| 4,379,925 A | * | 4/1983 | Grasselli et al. ............ 544/102 |
| 4,390,736 A | * | 6/1983 | Inoue et al. ................. 568/801 |
| 4,444,907 A | * | 4/1984 | Ohdan et al. ................ 502/211 |
| 4,456,563 A | * | 6/1984 | Katsumata et al. ... 260/465.8 R |
| 4,489,170 A | * | 12/1984 | Krabetz et al. ............. 502/211 |
| 4,504,677 A | * | 3/1985 | Sakamoto et al. .......... 562/534 |
| 4,530,916 A | | 7/1985 | Matsumoto et al. ........ 502/209 |
| 4,547,588 A | * | 10/1985 | Khoobiar .................... 562/535 |
| 4,558,028 A | * | 12/1985 | Tsuneki et al. ............. 502/211 |
| 4,564,607 A | * | 1/1986 | Yoneda et al. .............. 502/209 |
| 4,595,778 A | | 6/1986 | Duembgen et al. ......... 560/280 |
| 4,804,778 A | * | 2/1989 | Oh-Kita et al. ............. 562/534 |
| 4,892,856 A | | 1/1990 | Kawajiri et al. ............ 502/247 |
| 4,925,823 A | * | 5/1990 | Krabetz et al. ............. 502/211 |
| 4,925,980 A | | 5/1990 | Matsumoto et al. ........ 562/534 |
| 4,954,650 A | * | 9/1990 | Abe et al. .................... 562/534 |
| 4,985,592 A | | 1/1991 | Ishii et al. ................... 562/534 |
| 5,077,434 A | | 12/1991 | Sarumaru et al. ........... 562/534 |
| 5,087,744 A | * | 2/1992 | Krabetz et al. ............. 562/535 |
| 5,102,847 A | * | 4/1992 | Yamamoto et al. ......... 502/209 |
| 5,153,162 A | * | 10/1992 | Kurimoto et al. .......... 502/209 |
| 5,191,116 A | * | 3/1993 | Yamamatsu et al. ........ 562/549 |
| 5,206,431 A | * | 4/1993 | Hashiba et al. ............. 562/534 |
| 5,442,108 A | * | 8/1995 | Kawajiri et al. ............ 562/532 |
| 5,618,974 A | * | 4/1997 | Kurimoto et al. .......... 562/532 |
| 5,719,318 A | * | 2/1998 | Kawajiri et al. ............ 562/532 |
| 5,739,392 A | * | 4/1998 | Tanimoto et al. ........... 562/535 |
| 5,929,275 A | | 7/1999 | Wada et al. ................. 562/545 |
| 5,959,143 A | | 9/1999 | Sugi et al. ................... 562/534 |
| 6,028,220 A | | 2/2000 | Wada et al. ................. 562/546 |
| 6,429,332 B1 | * | 8/2002 | Tanimoto et al. ........... 562/532 |
| 6,462,232 B1 | * | 10/2002 | Nakamura et al. .......... 562/532 |

FOREIGN PATENT DOCUMENTS

| EP | 0 711 745 | 5/1996 |
| EP | 0 758 562 | 2/1997 |
| JP | 52-85091 | 7/1977 |
| JP | 8-206504 | 8/1996 |
| JP | 8-299797 | 11/1996 |
| JP | 9-316023 | 12/1997 |
| JP | 11-114418 | 4/1999 |
| JP | 11-343261 | 12/1999 |

* cited by examiner

Primary Examiner—Samuel S. Silverman
Assistant Examiner—Edward M. Johnson
(74) Attorney, Agent, or Firm—Nields & Lemack

(57) ABSTRACT

An object of the present invention is to provide a catalyst that is highly active and has a large mechanical strength. The catalyst of the present invention contains molybdenum, vanadium, copper and antimony as the essential components, being produced by using antimony acetate for an antimony source material and preferably used for producing acrylic acid by vapor-phase catalytic oxidation of acrolein.

19 Claims, No Drawings

CATALYST PROCESS OF MAKING

This application is a divisional of U.S. patent application Ser. No. 09/830,234 filed Apr. 24, 2001 now abandoned, the disclosure of which is hereby incorporated by reference.

TECHNICAL FIELD

The present invention relates to a novel catalyst, and more particularly to a catalyst suitable for use in the production of acrylic acid by vapor-phase catalytic oxidation of acrolein with molecular oxygen.

BACKGROUND ART

As a catalyst for the production of an unsaturated acid by vapor-phase catalytic oxidation of the unsaturated aldehyde, there are known, for examples, the catalyst obtained by tableting a catalytically active component composition, the catalyst obtained by molding a catalytically active component with auxiliary components into a globule or a ring, and the catalyst obtained by supporting a catalytically active component on inactive carriers with binders (hereinafter called coated catalyst).

For the preparation of the coated catalyst, Japanese Patent Laid-Open No.11709/1976 disclosed the method of coating by rolling the active component and the carriers in a rotating drum or jar; Japanese Patent Laid-Open No.153889/1977 disclosed the method of coating either by spraying the aqueous suspension of a preliminarily calcined active component over the carriers or by spreading the active component over vigorously moving carriers; and Japanese Patent Laid-Open No.85139/1989 disclosed the method of production using various granulators.

In the industrial plant for producing acrylic acid by vapor-phase catalytic oxidation of acrolein with molecular oxygen, the catalyst is packed into an as long as 5 m reaction tube from the upper side. Therefore, if the coated catalyst having a weak mechanical strength packed, the catalytically active components composition is peeled out and pulverized into powder and it cause a problem that they raise abnormally the pressure inside the tube during the reaction. So, the catalyst is demanded to have a large mechanical strength in property (such as little attrition resistance).

In recent years, the production of acrylic acid by vapor-phase catalytic oxidation of acrolein trends towards "high load reaction condition", that is, to increase the amount of acrolein supplied per unit volume of the catalyst. Since the oxidation reaction of acrolein is exothermic, such increased amount of acrolein brings about hot spots, which are likely to drive out the catalytic components including molybdenum, a constitutional element of the catalyst. As the defect, difference in pressure inside the reaction tube increases with the elapse of reaction time, decreasing the reaction merits (such as conversion of acrolein and acrylic acid yield) and blocking a long operation.

Such a situation demands to develop the highly active catalyst that would enable the operation at low reaction temperature. The present applicant made a diligent study to solve these problems, disclosing in Japanese Patent Laid-Open No.299797/1996 filed previous to the present application that the catalyst having a certain X-ray diffraction pattern was highly active and had a large mechanical strength. It also disclosed that it was preferable to use antimony trioxide subjected to no chemical treatment for an antimony-containing compound.

DISCLOSURE OF THE INVENTION

The present applicant has made another diligent study to solve these problems, finding to complete the present invention that the catalyst obtained by using a certain material is highly active for the oxidation reaction of acrolein and has a large mechanical strength. Namely, the present inventors have studied to reveals that antimony acetate used for the source material can provide the catalyst having larger mechanical strength, high activity and good reproducibility. The present invention relates to an antimony-containing molybdenum catalyst produced by using antimony acetate for an antimony source material, and more particularly to the followings:

(1) A catalyst in which the catalytically active component constitution is represented by the formula (1):

$$Mo_{12}V_aW_bCu_cSb_dX_eY_fZ_gO_h \qquad (1)$$

(in the formula, Mo, V, W, Cu, Sb and O represent molybdenum, vanadium, tungsten, copper, antimony and oxygen respectively; X represents at least one element selected from the group consisting of alkali metals and thalium; Y represents at least one element selected from the group consisting of magnesium, calcium, strontium, barium and zinc; Z represents at least one element selected from the group consisting of niobium, cerium, tin, chromium, manganese, iron, cobalt, samarium, germanium, titanium and arsenic; a, b, c, d, e, f, g and h represent atomic ratios of their respective elements, with $0<a\leq10$, $0\leq b\leq10$, $0<c\leq6$, $0<d\leq10$, $0\leq e\leq0.5$, $0\leq f\leq1$, $0\leq g<6$, based on 12 of molybdenum element; h is the number of oxygen atoms required to satisfy the total valence of the other elements), said catalytically active component composition comprising being produced by using antimony acetate for an antimony source material.

(2) A coated catalyst, wherein said catalyst is a coated catalyst obtained by coating said catalytically active component composition according to the above (1) on an inactive carrier, the coated catalyst obtained through the process including the following steps (a) to (c):

(a) Drying either an aqueous solution containing the catalytic component elements or an aqueous dispersion of compounds containing said elements, to prepare a catalytic component composition.

(b) Calcining the catalytic component composition obtained in step (a), to prepare a calcined powder.

(c) Coating the calcined powder obtained in step (b) on an inactive carrier, together with a binder and a strength-improvers if necessary.

(3) A coated catalyst according to the above (2), wherein the rate of a supported-calcined powder based on the total of said carrier and the calcined powder supported in the step (c) is 15 to 50%.

(4) A catalyst or coated catalyst according to any of the above (1) to (3), wherein said catalytically active component composition is what is produced through a step of spray drying either an aqueous solution containing the catalytic component elements or an aqueous dispersion of compounds containing said elements.

(5) A coated catalyst according to any of the above (2) to (4), wherein said catalytically active component composition is what is obtained by using ceramic fiber for said strength-improver in the step (c).

(6) A coated catalyst according to any of the above (2) to (5), wherein said catalytically active component composition is what is obtained by using crystalline cellulose for said binder in the step (c).

(7) A catalyst or coated catalyst according to any of the above (1) to (6), which comprises being used in the process for the production of acrylic acid by vapor-phase catalytic oxidation of acrolein with molecular oxygen.

The present invention will be described in detail below, where "part" and "%" mean "part by mass" and "% by mass" respectively unless otherwise defined.

There is no limitation to antimony acetate used for the source material in the present invention. Antimony acetate available on the market is satisfactory to use. The purity etc. unless it damages catalytic activity, has no problem to be solved. Antimony acetate having a purity of 95% and more is generally used. One having a purity of 99% and more is more preferable.

The atomic ratios of the respective elements in a catalytically active component of the present invention, if they are within the ranges as described in the above formula (1), have no problem to be solved. The more preferable ranges in the formula (1) are $2 \leq a \leq 5$, $0.2 \leq b \leq 2$, $0.2 \leq c \leq 4$, $0.3 \leq d \leq 4$, $0 \leq e \leq 0.2$, $0 \leq f \leq 0.5$, $0 \leq g \leq 3$. h, an atomic ratio of oxygen element, varies depending on atomic valences and atomic ratios of the other elements and is a value determined exclusively by the calcinations. The range is generally $42 \leq h \leq 133$, preferably $43 \leq h \leq 75$.

The catalyst of the present invention can be produced according to the conventional method for producing a molybdenum catalyst, except that antimony acetate is used for an antimony source material.

For example, at first, an aqueous solution containing the elements (hereinafter called catalytic components) in a catalytically active component composition as shown in formula (1) or an aqueous dispersion of compounds (catalytic component compounds) containing said elements is prepared. The aqueous solution or dispersion is hereinafter referred simply as "a slurry solution" unless otherwise specified. The slurry solution can be generally obtained by mixing the catalytic component compounds homogeneously in water to dissolve or disperse. The slurry solution in the present invention, if it is an aqueous solution, is most preferable. The catalytic component compounds are satisfactorily mixed in a formulation rate that the atomic ratios of the catalytic components fall within their respective ranges in the above formula (1).

The slurry solution can be produced by any procedure, for example, by making up catalytic component compounds into their respective solutions or dispersions, followed by mixing them; by dissolving or dispersing one or more catalytic component compounds to get plural solutions, followed by mixing them; or by making up all the catalytic component compounds into a solution or dispersion by one step.

The slurry solution is generally produced by preparing the A solution containing a molybdenum compound, a vanadium compound, a tungsten compound and antimony acetate and the B solution containing a copper compound, followed by mixing them. X component, Y component and Z component, if contained, are satisfactorily dissolved or dispersed in any adequate solution. Generally, X component and Y component are dissolved or dispersed in the B solution, and Z component is dissolved or dispersed in the A solution or the B solution suitably.

The amount of water used is not particularly limited as long as it is enough to produce the slurry solution, and suitably determined in view of method and temperature to select in a succeeding drying step. It is usually 200 to 2,000 parts by mass based on 100 parts of the total mass of compounds. Too little water cannot completely dissolve (or homogeneously mix) compounds. Too much water may bring about the problem of high energy-cost for drying step or incomplete drying.

The other catalytic component compounds used for producing the catalyst than antimony compound, provided that they can be converted into their respective oxides upon calcination, are not limited to the specific ones in the present invention. They include chlorides, sulfates, nitrates, ammonium salts and oxides of the other catalytic components than antimony. The illustrative examples include: molybdenum trioxide, molybdic acid and the salts thereof as a molybdenum compound; vanadium pentaoxide, vanadyl sulfate, vanadic acid and the salt thereof as a vanadium compound; tungstic acid and the salt thereof as a tungsten compound; and copper oxide, copper sulfate, copper nitrate and copper molybdate as a copper compound. These compounds may be used alone or as a mixture of two or more ones.

Then, the slurry solution is dried to give the dried powder (catalytic component composition) (step (a)).

The drying method, if it can dry completely the slurry solution, is not particularly limited, and includes drum drying, freeze-drying and spray drying. The spray drying is the most preferable in the present invention because it can dry to change the slurry state into the powder state in a short time. The drying temperature varies depending on a slurry solution concentration and a solution-feeding rate etc., and is about 85 to 130° C. at the outlet of a dryer. The drying is preferably carried out in such a way that it may give the dried powder having an average particle size of 20 to 100 μm.

The dried powder (catalytic component composition) as described above is calcined to give a catalytically active component (step (b)).

The calcination may be carried out before or after a shaping step. The dried powder may be calcined only before the shaping step as the case may be, but is preferably calcined by two steps, i.e. "preliminary calcination" before the shaping step and "primary calcination" after the shaping step as described below. The calcinations can be carried out by the known methods with no limitation.

When the dried powder is calcined by two steps, the preliminary calcination is generally carried out at a temperature of 250 to 500° C., preferably 300 to 450° C., for 1 to 15 hrs, preferably 3 to 6 hrs. The preliminary calcination step has an effect to provide a low attritional catalyst, which prevents the catalytically active component from pulverizing and peeling when a completed catalyst is packed in a reaction tube. The calcination product obtained by the preliminary calcination of the dried powder, including the further pulverized product, is hereinafter called a preliminary calcination powder in the present invention.

When the dried powder is calcined by two steps, the primary calcination is generally carried out at a temperature of 250 to 500° C., preferably 300 to 450° C., for 1 to 50 hrs. The primary calcinations, if the dried powder is shaped by tableting or by the other way than coating, is preferably carried out at a temperature of 250 to 500° C. for 1 to 50 hrs.

The catalysts of the present invention can be obtained either by shaping the above dried powder (catalytic component composition), followed by calcining; or by calcining the above dried powder to get the calcination powder (usually in a granule), which is then optionally pulverized, followed by shaping by a known adequate way, with further succeeding primary calcining if necessary. A shaping way is not particularly limited, and includes (I) compressing into a tablet, (II) mixing with shaping auxiliaries such as silica gel, diatomaceous earth and alumina powder, followed by extruding into a sphere or ring, and (III) coating and supporting on a carrier, preferably on a spherical carrier. The way (III) is preferable in the present invention, where it is desirable to coat the above calcination powder on the carrier together with binders and strength-improvers if necessary to get a coated catalyst [step (c)].

The coated catalyst, a preferable mode of catalyst in the present invention, will be described in detail below.

Tumbling granulation mentioned hereinafter is preferable for a coating step. This way is, for example, as follows. The flat or uneven disk mounted to the bottom of a fixed vessel rolls at a high speed, causing the carrier inside the vessel to take an axial rotation and an orbital revolution repeatedly so that it may be stirred vigorously. The mixture of a binder, the preliminary calcination powder and, if necessary, a shaping auxiliary and a strength-improver is added to the stirred carrier to coat the mixture on the carrier.

The binder may be added into the vessel: (1) as the previously blended mixture mentioned above, (2) when a mixture of the other ingredients is added, (3) after the mixture of the other ingredients is added, (4) before the mixture of the other ingredients is added, or (5) by dividing the mixture and the binder into their respective portions, followed by adding them in an adequately combined manner of (2) to (4) to make up the total mass. The manner (5) is preferably carried out by using an automatic feeder to control the addition rate so that a prescribed amount of mixture is supported on the carrier without the mixture adhered to the vessel wall and agglomerated by itself.

An illustration of the carrier includes spherical carriers made of, for example, silicone carbide, alumina, mullite or alundum that has a diameter of 2.5 to 10 mm, preferably 3 to 6 mm. Among these carriers, those having a porosity rate of 30 to 50% and a water-absorption rate of 10 to 30% are preferably used.

The ratio of the preliminary calcination powder used for coating on the carrier (supported-calcination powder) is generally 10 to 75%, preferably 15 to 50% relative to the total amount of the preliminary calcination powder and the carrier (supported-calcination powder+carrier).

The coated catalyst of the present invention, if it contains the powder for coating in a large ratio, has a higher reaction activity, but is likely to have a less mechanical strength (a large attrition rate). On the contrary, if it contains the powder for coating in a small ratio, it has a more mechanical strength (a less attrition rate), but is likely to have a lower reaction activity.

A binder is preferably used in the present invention when the preliminary calcination powder (the granule obtained by the preliminary calcinations or the pulverized product thereof) is coated on the carrier. The binder includes water, ethanol, polyhydric alcohol, a polymer binder such as polyvinyl alcohol, a cellulose such as crystalline cellulose, methyl cellulose and ethyl cellulose, and an inorganic binder such as aqueous silica sol solution. The preferable examples are the cellulose, a diol such as ethylene glycol, and a triol such as glycerin. The cellulose or an aqueous glycerin solution is preferable. The aqueous glycerin solution is generally used at a glycerin concentration of 5% or more, preferably 10 to 50%. Crystalline cellulose in the celluloses is particularly preferable. The cellulo makes to give a good shaping, resulting in improving the mechanical strength and the catalytic activity.

The amount of the binder used is generally 1 to 60 parts based on 100 parts of the preliminary calcination powder. The amount of the cellulose used for a binder is preferably 1 to 10 parts, more preferably 2 to 6 parts based on 100 parts of the preliminary calcination powder. The amount of aqueous glycerin solution used for a binder, if the concentration of the glycerin is for example 5 to 50%, is 10 to 30 parts, that is, 0.5 to 12 parts, preferably 1 to 8 parts in the amount of glycerin.

A shaping auxiliary such as silica gel, diatomaceous earth and alumina powder may be used if necessary in the present invention. The amount of shaping auxiliary used is generally 5 to 60 parts based on 100 parts of the preliminary calcination powder.

An inorganic fiber such as ceramic fiber and whisker may be used for a strength-improver if necessary, effecting to increase the mechanical strength of the catalyst. However, a fiber such as potassium titanate whisker and basic magnesium carbonate whisker is not preferable since it is reactive with the catalytic components. Ceramic fiber is particularly preferable. The amount of the fiber used is generally 1 to 30 parts based on 100 parts of the preliminary calcination powder.

The above shaping auxiliary and strength-improver are generally mixed with the preliminary calcination powder to use.

The coated product obtained by coating the preliminary calcination powder on a carrier has generally a diameter of 3 to 15 mm.

The coated product thus obtained can be calcined primarily to get the coated catalyst being an object. The primary calcinations is generally carried out at a temperature of 250 to 500° C., preferably 300 to 450° C., for 1 to 50 hrs. The primary calcination, when tableting or the other way than coating applies to a shaping method, is generally carried out at a temperature of 250 to 500° C. for 1 to 50 hrs.

A size of the coated catalyst is different by the carrier which is used and a coating amount of the catalyst etc. It is generally about 3 to 15 mm and preferably nearly same as a size of the carrier which is used or a little larger than that. The preferable size of the coated catalyst is 1.3 time of that of the carrier or less, preferably 1.2 time or less, further preferably 1.1 time or less.

EXAMPLES

The present invention will be described in more detail by way of the following examples and comparative examples. However, the present invention shall not be limited to these examples unless they are beyond the gist of the present invention.

Acrolein conversion, acrylic acid selectivity, and acrylic acid yield are defined by the following equations (2) to (4) respectively.

$$\text{Acrolein conversion (\% by mol)} = 100 \times (\text{acrolein reacted in mole})/(\text{acrolein supplied in mole}) \quad (2)$$

$$\text{Acrylic acid selectivity (\% by mol)} = 100 \times (\text{acrylic acid produced in mole})/(\text{acrolein converted in mole}) \quad (3)$$

$$\text{Acrylic acid yield (\% by mol)} = 100 \times (\text{acrylic acid produced in mole})/(\text{acrolein supplied in mole}) \quad (4)$$

Attrition resistance was measured with the tablet attrition resistance tester made by KAYAGAKI IRIKA KOGYO KK. A Catalyst sample put in the tester was rotated at 25 rpm for 10 min and screened through a 2.36 mm standard sieve. The mass of catalyst sample remaining on the sieve was determined to calculate the attrition resistance by the equation (5):

$$\text{Attrition resistance (\% by mass)} = 100 \times (\text{mass of sample put} - \text{mass of sample remaining on 2.36 mm sieve})/(\text{mass of sample put}) \quad (5)$$

Antimony acetate having a purity of 99.6% was used in the examples.

Example 1

In a formulating tank (A) equipped with a stirring motor, 600 parts of 95° C. deionized water and 16.26 parts of ammonium tungstate were put and stirred. 18.22 parts of ammonium metavanadate and 110 parts of ammonium molybdate were then added to dissolve. 7.75 parts of antimony acetate (purity 99.6%) was added further. In 96 parts of deionized water held in a formulating tank (B), 15.56 parts of copper sulfate was dissolved and the resultant solution was added into the formulating tank (A) to get a slurry solution.

The slurry solution was spray-dried under adjusting the feed rate so that the temperature at the outlet of a spray drier might be kept at about 100° C. The granule thus obtained was calcined (preliminary calcination) at 390° C. for about 5 hrs in a furnace, of which the temperature had been risen at a rate of about 60° C. per hour from the room temperature. Then, the granule thus obtained (hereinafter in the examples called preliminary calcination granule) was pulverized in a ball mill to get a powder (hereinafter in the examples called preliminary calcination powder).

In a tumble granulator, 12 parts of the preliminary calcination powder was placed on 36 parts of alundum carrier having a porosity rate of 40%, a water-absorption rate of 19.8% and a diameter of 4 mm while sprinkling 2.4 parts of 20% aqueous glycerin solution. The shaped product thus obtained was calcined at 390° C. for 5 hrs in a furnace, of which the temperature had been risen at a rate of about 70° C. per hour from the room temperature, to get a coated catalyst of the present invention. The coated catalyst had an almost same particle size as the carrier. The atomic ratio of a catalytically active component excluding oxygen in the coated catalyst thus obtained is as follows:

$$Mo_{12}V_3W_{1.2}Cu_{1.2}Sb_{0.5}$$

The attrition resistance of this coated catalyst was 0.1% or less.

30 ml of the coated catalyst thus obtained was packed into a reaction tube having an inner diameter of 21.4 mm.

Propylene was applied to the vapor-phase catalytic oxidation using a molybdenum-bismuth catalyst in a reaction bath containing heat medium to get a gas, to which oxygen and nitrogen were supplemented to obtain a composite gas as described below.

| | |
|---|---|
| Acrolein | 5.5% by volume |
| Unreacted propylene and the other organic compounds | 1.3% by volume |
| Oxygen | 7.4% by volume |
| Steam | 27.0% by volume |
| Inert gas including nitrogen | 58.8% by volume |

The composite gas was made to pass through the above reaction tube at a SV (Space Velocity: Volume of flowing gas per unit time/Volume of packed catalyst) of 1800/hr to react.

The results of reaction at a reaction bath temperature of 245° C. were as follows:
Acrolein conversion=99.2%
Acrylic acid selectivity=98.7%
Acrylic acid yield=97.9%

Comparative Example 1

A coated catalyst was obtained by the same way as described in Example 1, except that 3.78 parts of antimony trioxide was used in place of 7.75 parts of antimony acetate in Example 1. The atomic ratio of a catalytically active component excluding oxygen in the coated catalyst thus obtained is as follows:

$$Mo_{12}V_3W_{1.2}Cu_{1.2}Sb_{0.5}$$

The attrition resistance of this coated catalyst was 0.3%. The coated catalyst thus obtained was subjected to the reaction test in the same way as described in Example 1.

The results of reaction at a reaction bath temperature of 250° C. were as follows:
Acrolein conversion=99.1%
Acrylic acid selectivity=98.5%
Acrylic acid yield=97.6%

Example 2

23.1 parts of the preliminary calcination powder obtained in Example 1 was placed on 25 parts of alundum carrier having a porosity rate of 34%, a water-absorption rate of 17% and a diameter of 3.5 mm while sprinkling 3.1 parts of 20% aqueous glycerin solution. The shaped product thus obtained was calcined at 390° C. for 5 hrs in a furnace the temperature of which had been programmed to rise at a rate of about 70° C. per hour from the room temperature to get a coated catalyst of the present invention. The coated catalyst had an almost same particle size as the carrier. The atomic ratio of a catalytically active component excluding oxygen in the coated catalyst thus obtained is as follows:

$$Mo_{12}V_3W_{1.2}Cu_{1.2}Sb_{0.5}$$

The attrition resistance of this coated catalyst was 0.4%.

Comparative Example 2

A preliminary calcination powder was obtained by the same way as described in Example 1, except that 3.78 parts of antimony trioxide was used in place of 7.75 parts of antimony acetate in Example 1. 23.1 parts of the preliminary calcination powder thus obtained was placed on 25 parts of alundum carrier having a diameter of 3.5 mm while sprinkling 3.1 parts of 20% aqueous glycerin solution. The shaped product thus obtained was calcined at 390° C. for 5 hrs in a furnace the temperature of which had been programmed to rise at a rate of about 70° C. per hour from the room temperature to get a coated catalyst. A diameter of the coated catalyst was 3.7 mm. The atomic ratio of a catalytically active component excluding oxygen in the coated catalyst thus obtained is as follows:

$$M_{12}V_3W_{1.2}Cu_{1.2}Sb_{0.5}$$

The attrition resistance of this coated catalyst was 2.5%.

Example 3

15.4 parts of the preliminary calcination powder obtained in Example 1 was homogeneously mixed with 0.77 parts of crystalline cellulose. This mixed powder was placed on 36 parts of the same alundum carrier having a diameter of 3.5 mm as used in Example 2 while sprinkling 2.6 parts of 20% aqueous glycerin solution. The shaped product thus obtained was calcined at 390° C. for 5 hrs in a furnace the temperature of which had been programmed to rise at a rate of about 70° C. per hour from the room temperature to get a coated catalyst of the present invention. A diameter of the coated catalyst was 3.6 mm.
The attrition resistance of this coated catalyst was 0.2%. The coated catalyst thus obtained was subjected to the reaction test in the same way as described in Example 1.

The results of reaction at a reaction bath temperature of 235° C. were as follows:
Acrolein conversion=98.6%
Acrylic acid selectivity=98.9%
Acrylic acid yield=97.5%

Example 4

In a formulating tank (A) equipped with a stirring motor, 600 parts of 95° C. deionized water and 16.26 parts of ammonium tungstate were put and stirred. 18.22 parts of ammonium metavanadate and 110 parts of ammonium molybdate were then added to dissolve. 7.75 parts of antimony acetate was added further. In 96 parts of deionized water held in a formulating tank (B), 23.33 parts of copper sulfate and 1.05 parts of potassium nitrate were dissolved and the resultant solution was added into the formulating tank (A) to get a slurry solution.

The slurry solution was spray-dried under adjusting the feed rate so that the temperature at the outlet of a spray drier might be kept at about 100° C. to get a dried granule. The granule thus obtained was calcined at 390° C. for about 5 hrs in a furnace, of which the temperature had been risen at a rate of about 60° C. per hour from the room temperature.

The preliminary calcination granule thus obtained was pulverized in a ball mill to get a preliminary calcination powder. 12 parts of the preliminary calcination powder thus obtained was homogeneously mixed with 0.77 parts of crystalline cellulose.

The above mixed powder was placed on 36 parts of the same alundum carrier having a diameter of 4 mm as used in Example 1 while sprinkling 2.6 parts of 20% aqueous glycerin solution. The shaped product thus obtained was calcined at 390° C. for 5 hrs in a furnace, of which the temperature had been risen at a rate of about 70° C. per hour from the room temperature, to get a coated catalyst of the present invention. The atomic ratio of a catalytically active component excluding oxygen in the coated catalyst thus obtained is as follows:

$$Mo_{12}V_3W_{1.2}Cu_{1.8}Sb_{0.5}K_{0.2}$$

The diameter of the coated catalyst was almost the same as that of the carrier's.
The attrition resistance of this coated catalyst was 0.1% or less.
The coated catalyst was subjected to the reaction test in the same way as described in Example 1.
The results of reaction at a reaction bath temperature of 240° C. were as follows:
Acrolein conversion=98.6%
Acrylic acid selectivity=98.4%
Acrylic acid yield=97.0%

Example 5

A coated catalyst of the present invention was obtained by the same way as described in Example 3, except that no cellulose was used.

The atomic ratio of a catalytically active component excluding oxygen in the coated catalyst thus obtained is as follows:

$$Mo_{12}V_3W_{1.2}Cu_{1.8}Sb_{0.5}K_{0.2}$$

The attrition resistance of this coated catalyst was 0.1% or less.
The coated catalyst was subjected to the reaction test in the same way as described in Example 1.

The results of reaction at a reaction bath temperature of 245° C. were as follows:
Acrolein conversion=98.5%
Acrylic acid selectivity=98.1%
Acrylic acid yield=96.5%

Example 6

A coated catalyst of the present invention was obtained by the same way as described in Example 4, except that 3.99 parts of magnesium nitrate was used in place of 1.05 parts of potassium nitrate.

The atomic ratio of a catalytically active component excluding oxygen in the coated catalyst thus obtained is as follows:

$$Mo_{12}V_3W_{1.2}Cu_{1.8}Sb_{0.5}Mg_{0.3}$$

The attrition resistance of this coated catalyst was 0.1% or less.
The coated catalyst was subjected to the reaction test in the same way as described in Example 1.
The results of reaction at a reaction bath temperature of 245° C. were as follows:
Acrolein conversion=98.7%
Acrylic acid selectivity=98.0%
Acrylic acid yield=96.7%

Example 7

In a formulating tank (A) equipped with a stirring motor, 600 parts of 95° C. deionized water and 16.26 parts of ammonium tungstate were put and stirred. 18.22 parts of ammonium metavanadate and 110 parts of ammonium molybdate were then added to dissolve. 7.75 parts of antimony acetate was added further. After 20 min, 2.07 parts of niobium oxide was added. In 96 parts of deionized water held in a formulating tank (B), 15.05 parts of copper nitrate was dissolved and the resultant solution was added into the formulating tank (A) to get a slurry solution.

The slurry solution was spray-dried under adjusting the feed rate so that the temperature at the outlet of a spray drier might be kept at about 100° C. to get a dried granule. The granule thus obtained was calcined at 370° C. for about 5 hrs in a furnace, of which the temperature had been risen at a rate of about 60° C. per hour from the room temperature.

The preliminary calcination granule thus obtained was pulverized in a ball mill to get a preliminary calcination powder. 12 parts of the preliminary calcination powder thus obtained was homogeneously mixed with 0.77 parts of crystalline cellulose.

The above mixed powder was placed on 36 parts of the same alundum carrier having a diameter of 4 mm as used in Example 1 while sprinkling 2.7 parts of 6% aqueous glycerin solution. The shaped product thus obtained was calcined at 390° C. for 5 hrs in a furnace, of which the temperature had been risen at a rate of about 70° C. per hour from the room temperature, to get a coated catalyst of the present invention. The atomic ratio of a catalytically active component excluding oxygen in the coated catalyst thus obtained is as follows:

$$Mo_{12}V_3W_{1.2}Cu_{1.2}Sb_{0.5}Nb_{0.3}$$

The attrition resistance of this coated catalyst was 0.1% or less.
The coated catalyst was subjected to the reaction test in the same way as described in Example 1.

The results of reaction at a reaction bath temperature of 243° C. were as follows:
  Acrolein conversion=99.0%
  Acrylic acid selectivity=98.4%
  Acrylic acid yield=97.4%

Example 8

In a formulating tank (A) equipped with a stirring motor, 600 parts of 95° C. deionized water and 16.26 parts of ammonium tungstate were put and stirred. 18.22 parts of ammonium metavanadate and 110 parts of ammonium molybdate were then added to dissolve. 7.75 parts of antimony acetate was added further. In 96 parts of deionized water held in a formulating tank (B), 15.56 parts of copper sulfate, 0.52 parts of potassium nitrate and 4.19 parts of ferric nitrate were dissolved and the resultant solution was added into the formulating tank (A) to get a slurry solution.

The slurry solution was spray-dried under adjusting the feed rate so that the temperature at the outlet of a spray drier might be kept at about 100° C. to get a dried granule. The granule thus obtained was calcined at 370° C. for about 5 hrs in a furnace, of which the temperature had been risen at a rate of about 60° C. per hour from the room temperature.

The preliminary calcination granule thus obtained was pulverized in a ball mill to get a preliminary calcination powder. 12 parts of the preliminary calcination powder thus obtained was homogeneously mixed with 0.77 parts of crystalline cellulose.

The above mixed powder was placed on 36 parts of the same alundum carrier having a diameter of 4 mm as used in Example 1 while sprinkling 2.6 parts of 20% aqueous glycerin solution. The shaped product thus obtained was calcined at 390° C. for 5 hrs in a furnace, of which the temperature had been risen at a rate of about 70° C. per hour from the room temperature, to get a coated catalyst of the present invention. The atomic ratio of a catalytically active component excluding oxygen in the coated catalyst thus obtained is as follows:

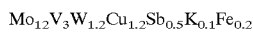

$Mo_{12}V_3W_{1.2}Cu_{1.2}Sb_{0.5}K_{0.1}Fe_{0.2}$

The attrition resistance of this coated catalyst was 0.1% or less.
The coated catalyst was subjected to the reaction test in the same way as described in Example 1.
The results of reaction at a reaction bath temperature of 243° C. were as follows:
  Acrolein conversion=98.7%
  Acrylic acid selectivity=98.7%
  Acrylic acid yield=97.4%

Example 9

18 parts of the preliminary calcination powder obtained in Example 1 was homogeneously mixed with 0.9 parts of silica alumina fiber having an average fiber length of 100 μm as well as an average fiber diameter of 2.0 μm and 0.54 parts of methyl cellulose. In a tumble granulator, the above mixed powder was placed on 35.1 parts of the same alundum carrier having a diameter of 3.5 mm as used in Example 2 while sprinkling 2.8 parts of 20% aqueous glycerin solution. The shaped product thus obtained was calcined at 390° C. for 2.5 hrs in a furnace, of which the temperature had been risen at a rate of about 70° C. per hour from the room temperature, to get a coated catalyst of the present invention. The attrition resistance of this coated catalyst was 0.1% or less.

The coated catalyst was subjected to the reaction test in the same way as described in Example 1.
The results of reaction at a reaction bath temperature of 230° C. were as follows:
  Acrolein conversion=99.4%
  Acrylic acid selectivity=98.4%
  Acrylic acid yield=97.8%

INDUSTRIAL APPLICABILITY

A catalyst of the present invention, especially the coated catalyst can be used in the process for producing an unsaturated acid from the unsaturated aldehyde as a source material, preferably in the process for producing acrylic acid from acrolein as the source material.

The catalyst of the present invention is industrially valuable because it has a large mechanical strength enough to pack in a reaction tube with the catalytically active component little peeled and pulverized and because it has a high acrylic acid selectivity enough to cope with a high load reaction condition.

What is claimed is:

1. A process for producing a catalyst whose catalytically active component having a composition represented by the formula (1):

$$Mo_{12}V_aW_bCu_cSb_dX_eY_fZ_gO_h \qquad (1)$$

wherein Mo, V, W, Cu, Sb and O represent molybdenum, vanadium, tungsten, copper, antimony and oxygen, respectively; X represents at least one element selected from the group consisting of alkali metals and thallium; Y represents at least one element selected from the group consisting of magnesium, calcium, strontium, barium and zinc; Z represents at least one element selected from the group consisting of niobium, cerium, tin, chromium, manganese, iron, cobalt, samarium, germanium, titanium and arsenic; a, b, c, d, e, f, g and h represent atomic ratios of their respective elements, with $0<a\leq10$, $0\leq b\leq10$, $0<c\leq6$, $0<d\leq10$, $0\leq e\leq0.5$, $0\leq f\leq1$, $0\leq g<6$, based on 12 molybdenum atoms; and h is a number of oxygen atoms required to satisfy the total valence of the other elements, said process comprising preparing a slurry solution for the catalyst containing antimony acetate as an antimony material for the catalyst.

2. A process for producing a coated catalyst, obtained by coating the catalytically active component composition according to claim 1 on an inactive carrier, comprising the following steps (a) to (c):
  (a) Drying either an aqueous solution or a dispersion containing the compounds of the catalytic component elements, wherein the aqueous solution or dispersion contains antimony acetate as an antimony material, thus obtaining a catalytic component composition;
  (b) Calcining the catalytic component composition obtained in step (a), thus obtaining a calcined powder;
  (c) Coating the calcined powder obtained in step (b) on the carrier, together with a binder and, optionally, a strength-improver.

3. The process according to claim 2, wherein a supported-calcined powder has 15 to 50% by mass race based on the total amount of said carrier and said calcined powder in step (c).

4. The process according to any of claims 2 or 3, wherein said drying in step (a) is spray-drying.

5. The process according to any of claims 2 or 3, wherein said strength-improver in step (c) is ceramic fiber.

6. The process according to any of claims 2 or 3, wherein said binder in step (c) is crystalline cellulose.

7. The process for producing a catalyst or coated catalyst according to any of claims 1, 2 or 3, wherein the catalyst is used in a process for the production of acrylic acid by vapor-phase catalytic oxidation of acrolein with molecular oxygen.

8. The process according to claim 4, wherein said strength-improver in step (c) is ceramic fiber.

9. The process according to claim 4, wherein said binder in step (c) is crystalline cellulose.

10. The process according to claim 5, wherein said binder in step (c) is crystalline cellulose.

11. The process according to claim 8, wherein said binder in step (c) is crystalline cellulose.

12. The process for producing a catalyst or coated catalyst according to claim 4, wherein the catalyst is used in a process for the production of acrylic acid by vapor-phase catalytic oxidation of acrolein with molecular oxygen.

13. The process for producing a catalyst or coated catalyst according to claim 5, wherein the catalyst is used in a process for the production of acrylic acid by vapor-phase catalytic oxidation of acrolein with molecular oxygen.

14. The process for producing a catalyst or coated catalyst according to claim 6, wherein the catalyst is used in a process for the production of acrylic acid by vapor-phase catalytic oxidation of acrolein with molecular oxygen.

15. The process for producing a catalyst or coated catalyst according to claim 8, wherein the catalyst is used in a process for the production of acrylic acid by vapor-phase catalytic oxidation of acrolein with molecular oxygen.

16. The process for producing a catalyst or coated catalyst according to claim 9, wherein the catalyst is used in a process for the production of acrylic acid by vapor-phase catalytic oxidation of acrolein with molecular oxygen.

17. The process for producing a catalyst or coated catalyst according to claim 10, wherein the catalyst is used in a process for the production of acrylic acid by vapor-phase catalytic oxidation of acrolein with molecular oxygen.

18. The process for producing a catalyst or coated catalyst according to claim 11, wherein the catalyst is used in a process for the production of acrylic acid by vapor-phase catalytic oxidation of acrolein with molecular oxygen.

19. A process for producing a catalyst according to claim 1, wherein antimony acetate having purity of 99% of more is used to prepare said slurry solution containing antimony acetate.

* * * * *